(12) United States Patent
Kinder, Jr. et al.

(10) Patent No.: US 6,734,177 B2
(45) Date of Patent: May 11, 2004

(54) CERTAIN SALTS OF DISCODERMOLIDE ACID, PHARMACEUTICAL COMPOSITIONS CONTAINING THEM AND THEIR USE IN TREATING TUMORS

(75) Inventors: Frederick R. Kinder, Jr., Morristown, NJ (US); Prasad K. Kapa, Parsippany, NJ (US); Eric M. Loeser, Lake Hiawatha, NJ (US)

(73) Assignee: Novartis AG, Basel (CH)

( * ) Notice: Subject to any disclaimer, the term of this patent is extended or adjusted under 35 U.S.C. 154(b) by 23 days.

(21) Appl. No.: 10/122,812

(22) Filed: Apr. 15, 2002

(65) Prior Publication Data

US 2003/0032641 A1 Feb. 13, 2003

Related U.S. Application Data

(60) Provisional application No. 60/284,412, filed on Apr. 17, 2001.

(51) Int. Cl.[7] .................... C07D 295/37; C07D 295/03; A61K 31/535; A61K 31/495; A61P 35/02
(52) U.S. Cl. .............................. 514/212.01; 514/231.2; 514/239.5; 514/315; 514/317; 514/408; 514/529; 540/450; 540/484; 544/107; 544/108; 544/401; 544/403; 544/404; 546/187; 548/579; 548/400; 562/166
(58) Field of Search ................................ 540/450, 484; 544/107, 108, 403, 404, 401; 546/187; 548/578, 579, 400; 562/166; 514/231.2, 239.5, 212.01, 529, 315, 317, 408

(56) References Cited

FOREIGN PATENT DOCUMENTS

| GB | 2 280 677 A | 2/1995 |
|---|---|---|
| WO | WO 98/24429 | 6/1998 |
| WO | WO 00/04865 | 2/2000 |

OTHER PUBLICATIONS

Paterson I. et al., "Total Synthesis of the Antimicrotubule Agent (+)–Discodermolide Using Boron–Mediated Aldol Reactions of Chiral Ketones", Agnew.Chem.Int.Ed., vol. 39, No. 2, pp. 377–380 (2000).
Smith A.B. et al., "Gram–Scale Synthesis of (+)–Discodermolide", Organic Letters, Vo1, No. 11, pp. 1823–1826 (1999).
Filla S.A. et al., "Synthesis of C1–C8 and C9–C24 fragments of (–)–discodermolide: use of asymmetric alkylation and stereoselective aldol reactions", Tetrahedron Letters, vol. 40, No. 30, pp. 5449–5453 (1999).
Marshall J.A. et al., "Total Synthesis of (+)–Discodermolide", J.Org.Chem., vol. 63, No. 22, pp. 7885–78982 (1998).
Hung D.T. et al., "Syntheses of Discodermolides Useful for Investigating Microtubule Binding and Stabilization", J.American Chemical Society, vol. 118, No. 45, pp. 11054–11080 (1996).
Smith, A.B. et al., "Total Synthesis of (–)–Discodermolide", J.Am.Chem.Soc., vol. 117, No. 48, pp. 12011–12012 (1995).
Halstead, D.A., "Total Synthesis of (–)–Miyakolide. II. Total Synthesis of (–)–Discodermolide. III. Total Synthesis of (+)–Discodermolide", vol. 60/03–B of Dissertation Abstracts International. p.1087 (1999).
Harried, S.S., "A Total Synthesis of (–)–Discodermolide (Alkylation, Antitumor)", vol. 59/11–B of Dissertation Abstracts International. p. 5854 (1998).

*Primary Examiner*—Mark L. Berch
*Assistant Examiner*—Kahsay Habte
(74) *Attorney, Agent, or Firm*—Joseph J. Borovian

(57) ABSTRACT

The present invention relates to certain salts of discodermolide acid, pharmaceutical compositions containing said salts, the use of said salts in treating tumors and to a process for making said salts.

18 Claims, No Drawings

CERTAIN SALTS OF DISCODERMOLIDE ACID, PHARMACEUTICAL COMPOSITIONS CONTAINING THEM AND THEIR USE IN TREATING TUMORS

This application claims the benefit of provisional Application No. 60/284,412 filed Apr. 17, 2001, the contents of which are incorporated herein by reference.

FIELD OF THE INVENTION

The present invention relates to the area of chemotherapeutic agents and, more particularly, relates to certain salts of discodermolide acid, and the use of said discodermolide acid salts in treating tumors.

BACKGROUND OF THE INVENTION

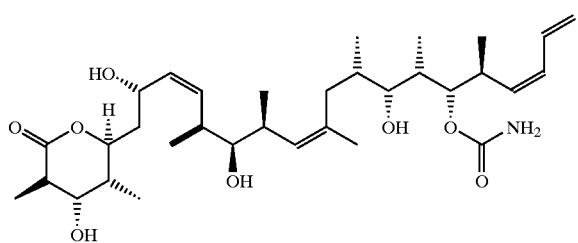

1

Discodermolide (1) is a novel polyketide natural product that was isolated from extracts of the marine sponge *Discodermia dissolute* by researchers at the Harbor Branch Oceanographic Institution (HBOI) (Gunasekera S P, Gunasekera M, Longley R E, Schulte G K. Discodermolide: a new bioactive polyhydroxylated lactone from the marine sponge *Discodermia dissolute*. [published erratum appears in J. Org. Chem. 1991;56:1346]. J. Org. Chem. 1990;55:4912–15.). Discodermolide lacks obvious structural resemblance to palitaxel, yet it shares with paclitaxel (the active substance in the drug Taxol) the ability to stabilize microtubules. In mechanism-based assays, discodermolide is more effective than paclitaxel. In fact, of the handful of compounds known to induce polymerization of purified tubulin, discodermolide is the most potent. However, microtubules, the major structural component in cells, are not simple equilibrium polymers of tubulin. They exist as regulated GTP-driven dynamic assemblies of heterodimers of $\alpha$ and $\beta$ tubulin. Although the dynamics are relatively slow in interphase cells, upon entering mitosis, the rate of growing and shortening increases 20 to 100-fold—the average microtubule turns over half the tubulin subunits every ten seconds. This change in rate allows the cytoskeletal microtubule network to dismantle and a bipolar spindle-shaped array of microtubules to assemble. The spindle attaches to chromosomes and moves them apart. The response to complete suppression of microtubule dynamics in cells is death. However, mitotic cells are more sensitive and the tolerance threshold appears to be cell-type specific. Molecules like paclitaxel that bind with high affinity to microtubules disrupt the dynamics process in tumor cells with lethal results even when the ratio of bound drug to tubulin is very low. Discodermolide binds to tubulin competitively with paclitaxel. Since paclitaxel has proven to be useful in treating some cancers, other compounds of the same mechanistic class may have utility against hyperproliferative disorders.

DESCRIPTION OF THE PRIOR ART

Preparation of intermediates for the synthesis of discodermolides and their polyhydroxy dienyl lactone derivatives for pharmaceutical use. Smith, Amos B. Iii; Qiu, Yuping; Kaufman, Michael; Arimoto, Hirokazu; Jones, David R.; Kobayashi, Kaoru; Beauchamp, Thomas J. (The Trustees of the University of Pennsylvania, USA). PCT Int. Appl. (2000), 201 pp. CODEN: PIXXD2 WO 0004865 A2 20000203 Designated States W: AU, CA, JP. Designated States RW: AT, BE, CH, CY, DE, DK, ES, Fl, FR, GB, GR, IE, IT, LU, MC, NL, PT, SE. Patent written in English. Application: WO 99-US16369 19990720. Priority: US 98-121551 19980723. CAN 132:137207 AN 2000:84572

Total synthesis of the antimicrotubule agent (+)-discodermolide using boron-mediated aldol reactions of chiral ketones. Paterson, Ian; Florence, Gordon J.; Gerlach, Kai; Scott, Jeremy. Univ. Chem. Lab., Cambridge, UK. Angew. Chem., Int. Ed. (2000), 39(2), 377–380. CODEN: ACIEF5 ISSN: 1433–7851. Journal written in English. CAN 132:236926 AN 2000:76529

Gram-Scale Synthesis of (+)-Discodermolide. Smith, Amos B., III; Kaufman, Michael D.; Beauchamp, Thomas J.; LaMarche, Matthew J.; Arimoto, Hirokazu. Department of Chemistry Monell Chemical Senses Center and Laboratory for Research on the Structure of Matter, University of Pennsylvania, Pa., USA. Org. Lett. (1999), 1(11), 1823–1826. CODEN: ORLEF7 ISSN: 1523-7060. Journal written in English. CAN 132:35548 AN 1999:694867

Total synthesis of (+)-miyakolide. I. Total synthesis of (-)-discodermolide. II. Total synthesis of (+)-discodermolide. Halstead, David Patrick. Harvard Univ., Cambridge, Mass., USA. Avail. UMI, Order No. DA9921509. (1999), 199 pp. From: Diss. Abstr. Int., B 1999, 60(3), 1087. Dissertation written in English. CAN 132:194227 AN 1999:567611

Synthesis of C1–C8 and C9–C24 fragments of (-)-discodermolide: use of asymmetric alkylation and stereoselective aldol reactions. Filla, Sandra A.; Song, Jinhua J.; Chen, Lihren; Masamune, Satoru. Department of Chemistry, Massachusetts Institute of Technology, Cambridge, Mass., USA. Tetrahedron Lett. (1999), 40(30), 5449–5453. CODEN: TELEAY ISSN: 0040-4039. Journal written in English. CAN 131:271758 AN 1999:461996

A total synthesis of (-)-discodermolide. Harried, Scott S. Univ. of California, Los Angeles, Calif., USA. Avail. UMI, Order No. DA9913066. (1998), 189 pp. From: Diss. Abstr. Int., B 1999, 59(11), 5854. Dissertation written in English. CAN 131:199544 AN 1999:320599

Total Synthesis of (+)-Discodermolide. Marshall, James A.; Johns, Brian A. Department of Chemistry, University of Virginia, Charlottesville, Va., USA. J. Org. Chem. (1998), 63(22), 7885–7892. CODEN: JOCEAH ISSN: 0022-3263. Journal written in English. CAN 130:38235 AN 1998:642722

Synthetic techniques and intermediates for polyhydroxy, dienyllactones and mimics thereof. Smith, Amos B., III; Qiu, Yuping; Kaufman, Michael; Arimoto, Hirokaza; Jones, David R.; Kobayashi, Kaoru. (Trustees of the University of Pennsylvania, USA). PCT Int. Appl. (1998), 194 pp. CODEN: PIXXD2 WO 9824429 A1 19980611 Designated States W: CA, JP. Designated States RW: AT, BE, CH, DE, DK, ES, FI, FR, GB, GR, IE, IT, LU, MC, NL, PT, SE. Patent written in English. Application: WO 97-US21798 19971201. Priority: US 96-759817 19961203. CAN 129:67649 AN 1998:394202

Syntheses of Discodermolides Useful for Investigating Microtubule Binding and Stabilization. Hung, Deborah T.; Nerenberg, Jennie B.; Schreiber, Stuart L. Howard Hughes Medical Institute, Harvard University, Cambridge, Mass., USA. J. Am. Chem. Soc. (1996), 118(45), 11054–11080. CODEN: JACSAT ISSN: 0002-7863. Journal written in English. CAN 126:31209 AN 1996:657111

Total Synthesis of (−)-Discodermolide. Smith, Amos B., III; Qiu, Yuping; Jones, David R.; Kobayashi, Kaoru. Monell Chemical Senses Center, University of Pennsylvania, Philadelphia, Pa., USA. J. Am. Chem. Soc. (1995), 117(48), 12011–12. CODEN: JACSAT ISSN: 0002-7863. Journal written in English. CAN 124:86679 AN 1995:938846

Total synthesis of discodermolide. Golec, Julian Marian Charles; Jones, Stuart Donald; Gillespie, Roger John. (Roussel Laboratories Ltd., UK). Brit. UK Pat. Appl. (1995), 57 pp. CODEN: BAXXDU GB 2280677 A1 19950208 Patent written in English. Application: GB 94-15399 19940729. Priority: GB 93-15802 19930730. CAN 123:32864 AN 1995:615210

SUMMARY OF THE INVENTION

The present invention provides new anti-tumor agents which are effective against a variety of cancer cells. More particularly, the present invention relates to certain discodermolide acid salts which exhibit a higher degree of selectivity in killing cancer cells. In addition, the present invention provides pharmaceutical compositions useful in treating tumors comprising a therapeutically effective amount of certain discodermolide acid salts. Moreover, the present invention provides a method of treating tumors comprising administering to a mammal afflicted therewith a therapeutically effective amount of certain discodermolide acid salts. Furthermore, the present invention relates to a process for preparing certain discodermolide acid salts.

DETAILED DESCRIPTION OF THE INVENTION

The essence of the instant invention is the discovery that certain discodermolide acid salts are useful in treating tumors. In one embodiment, the instant invention provides new anti-tumor agents of formula I

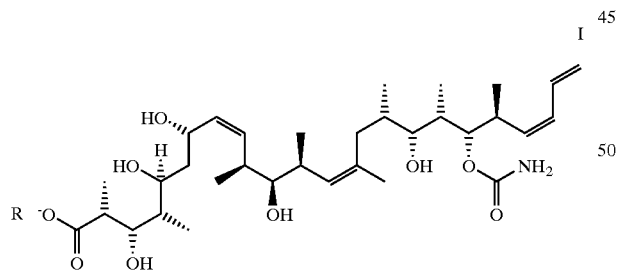

I where R is $Li^+$, $Na^+$, $K^+$, $½Ca^{++}$, $½Mg^{++}$, $½Mn^{++}$, $R_1R_2R_3R_4N^+$, or a nitrogen containing ring selected from

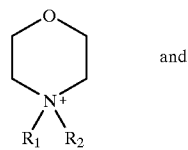

II

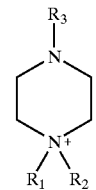

III and

IV where each of $R_1$, $R_2$, $R_3$ and $R_4$, independently, is hydrogen, $(C_{1-12})$alkyl, hydroxy$(C_{2-8})$alkyl or benzyl; and n is 1–5.

Preferred compounds are those of formula I where
R is $Li^+$, $Na^+$, $K^+$, $½Ca^{++}$, $R_1R_2R_3R_4N^+$, or a nitrogen containing ring selected from II, III and IV
where each of $R_1$, $R_2$, $R_3$ and $R_4$, independently, is hydrogen, $(C_{1-8})$alkyl, hydroxy$(C_{2-6})$alkyl or benzyl; and n is 1–3.

More preferred compounds are those of formula I where
R is $Na^+$, $K^+$, $½Ca^{++}$, $R_1R_2R_3R_4N^+$, or a nitrogen containing ring selected from II and III;
where each of $R_1$, $R_2$, $R_3$ and $R_4$, independently, is hydrogen, $(C_{1-6})$alkyl, hydroxy$(C_{2-4})$alkyl or benzyl; and n is 1 or 2.

Even more preferred compounds are those of formula I where
R is $Na^+$, $½Ca^{++}$, $R_1R_2R_3HN^+$, or a nitrogen containing ring selected from

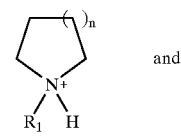

IIa and

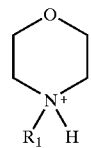

IIIa where each of $R_1$, $R_2$ and $R_3$, independently, is hydrogen, $(C_{1-6})$alkyl, hydroxyethyl or benzyl; and n is 1 or 2.

In another embodiment, the instant invention provides pharmaceutical compositions useful in treating tumors comprising a pharmaceutically acceptable carrier or diluent and a therapeutically effective amount of a compound of formula I above.

In still another embodiment, the instant invention provides a method for treating tumors comprising administering to a mammal in need of such treatment a therapeutically effective amount of a compound of formula I above.

In the above definitions: the term "$(C_{1-12})$alkyl" as used herein refers to a straight, branched, or cycloalkyl group consisting solely of carbon and hydrogen and having from 1 to 12 carbon atoms. Examples of "alkyl" groups include methyl, ethyl, propyl, butyl, pentyl, 3-methypentyl, cyclohexyl, cyclopentylbutyl, etc. The "$(C_{1-8})$alkyl" portion of hydroxy$(C_{1-8})$alkyl as used herein refers to a straight or branched group consisting solely of carbon and hydrogen and having from 1 to 8 carbon atoms.

Discodermolide acid salts may be prepared from discodermolide of formula 1 as depicted below:

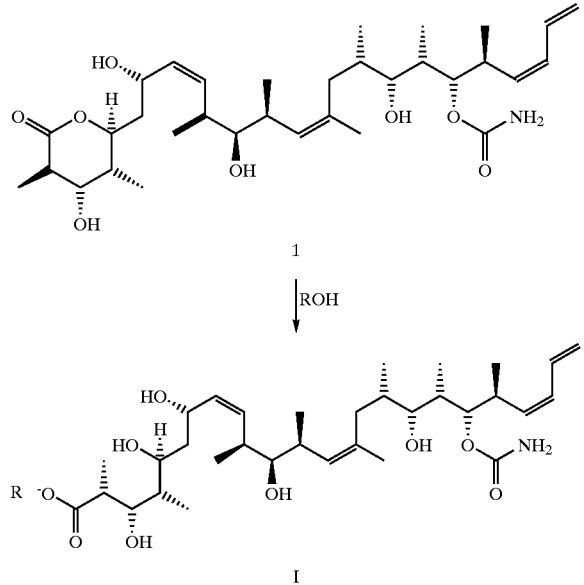

where each R is as defined above.

The preparation of the discodermolide acid salt involves the hydrolysis of 1. The hydrolysis requires between 1 and 100 equivalents of 1 relative to ROH, preferably between 1 and 5 equivalents of I relative to ROH. The hydrolysis is conducted in the presence of a polar organic solvent, preferably an ether, more preferably tetrahydrofuran, at a temperature of between 0° C. and 20° C., preferably between 0° C. and 10° C., for a period of between 5 minutes and 2 hours, preferably for a period between 15 and 30 minutes.

All of the compounds ROH are either known and disclosed in the literature or may be prepared analogous to procedures disclosed in the literature.

If desired, the discodermolide acid salt obtained may be purified by conventional techniques such as chromatography or recrystallization (if a solid).

As is evident to those skilled in the art, compounds of formula I contain asymmetric carbon atoms. It should be understood, therefore, that the individual stereoisomers are contemplated as being included within the scope of this invention.

As indicated above, all of the compounds of formula I are anti-tumor agents and are, therefore, useful in inhibiting the growth of various lymphomas, sarcomas, carcinomas, myelomas, and leukemia cell lines. The anti-tumor activity of the compounds of formula I may be demonstrated employing the Anchorage Dependent Growth Monolayer Assay (ADGMA) which measures the growth inhibitory effects of test compounds on proliferation of adherent cell monolayers. This assay was adapted from the 60 cell line assay used by the National Cancer Institute (NCI) with the following modifications:

1) four cell lines representative for the important tumor types, viz., MIP 101 colon carcinoma, HCT 116 colon carcinoma, 1A9 ovarian carcinoma and 1A9PTX22 ovarian carcinoma were utilized; and 2) a tetrazolium derivative, viz., MTT, was utilized to determine cell density.

The ADGMA compares the number of viable cells following a 3-day exposure to a test compound relative to a number of cells present at the time the test compound was added. Cell viability is measured using a tetrazolium derivative, viz., 3-[4,5-dimethylthiazol-2-yl]-2,5-diphenyl-tetrazolium bromide (MTT) that is metabolically reduced in the presence of an electron coupling agent (PMS; phenazine methosulfate) by viable cells to a water-soluble formazan derivative. The absorbence at 540 nm (A540) of the formazan derivative is proportional to the number of viable cells. The $IC_{50}$ for a test compound is the concentration of compound required to reduce the final cell number to 50% of the final control cell number. If cell proliferation is inhibited, the assay further defines compounds as cytostatic (cell number after 3-day compound incubation>cell number at time of compound addition) or cytotoxic (cell number after 3-day compound incubation<cell number at time of compound addition).

The HCT 116 colon carcinoma cell line was obtained from the American Type Culture Collection (ATCC, Rockville, Md.). The MIP 101 colon carcinoma was obtained from Dr. Robert Kramer (Bristol Meyers Squibb) and was previously described (Niles R M, Wilhelm S A, Steele G D JR, Burke B, Christensen T, Dexter D, O'Brien M J, Thomas P, Zamcheck N. Isolation and characterization of an undifferentiated human colon carcinoma cell line (MIP-101). Cancer Invest. 1987;5(6):545–52.). The 1A9 and the 1A9PTX22 ovarian tumor cell lines were obtained from Dr. Tito Fojo, Medicine Branch, Division of Clinical Sciences, National Cancer Institute, National Institutes of Health, Bethesda, Md. 20892. The 1A9 is a clone of the ovarian carcinoma cell line, A2780 (Giannakakou P, Sackett, D L, Kang Y -K, Zhan Z, Buters J T M, Fojo T, Poruchynsky M S. Paclitaxel-resistant human ovarian cancer cells have mutant β-tubulins that impaired paclitaxel-driven polymerization. J. Biol. Chem. 1997, 272(4):17118–17125). The 1A9PTX22 subline was isolated as an individual clone from the 1A9 cell line in a single step selection by exposure to 5 ng/mL paclitaxel in the presence of 5 μg/mL of verapamil. All cell lines were used between passages 4–20 following thawing. MIP 101 colon carcinoma, HCT 116 colon carcinoma, 1A9 ovarian carcinoma and 1A9PTX22 ovarian carcinoma cell lines are maintained and plated in RPMI 1640 medium containing 10% fetal bovine serum.

Cells are trypsinized and counted using hemacytometer to determine cell concentrations. Cells were then plated in their respective maintenance media (200 μL/well) in 96-well plates at the following concentrations: MIP 101, 2000 cells/well, HCT 116, 2000 cells/well, 1A9, 10000 cells/well, and 1A9PTX22, 10000 cells/well. The number of cells/well was determined in preliminary experiments, and resulted in 75–90% of confluency by day 4 after plating. Initial cell densities, assayed one day after plating, are roughly 0.10–0.20 A540 absorbence units greater than the media blank. Ninety six well plates were seeded on day 0 and the test compounds are added on day 1. A "time 0" plate was created that received media only in row A and one cell line/row in rows B–E. The "time 0" plate was processed 24 hours after plating (at the time when drugs were added to experimental plates), as follows: To each well 5 microliters of the MTT stock solution (0.5 mg/ml in PBS) was added to each well and then incubated for three hours at 37 degrees C., 5% CO2, in a humidified environment. Media was then carefully and completely removed. Plates were allowed to dry in the dark. DMSO (dimethylsulfoxide) was added to each well (100 μl/well) and plates were placed on an orbital shaker for 2 hours. Plates were read in the 96-well plate reader at 540 nm in a Molecular Devices plate reader utilizing Softmax Version 2.35 in absorbence mode-endpoint L-1, using DMSO as a blank. One day following plating, test compounds were added (in a final 1:10 dilution) to the test plates and subsequently serial diluted 10 times. The control plate received 1:10 dilution of the solvent (10% DMSO/90% RPMI 1640) only. Three days after addition of test compounds all the experimental plates and the control plate were processed as described above for the "time 0" plate. $IC_{50}$ values are determined from graphs of percent net growth as a function of compound concentration. Percent net growth is calculated as (Cell+Drug $A_{540}$–Initial 540/Cell+Drug Vehicle 540–Initial 540).

The following $IC_{50}$ values (average±S.E.M.) in μM were obtained:

| Compound | MIP101 | HCT116 | 1A9 | 1A9PTX22 |
| --- | --- | --- | --- | --- |
| Ex. 1 | 0.3 ± 0.01 | 0.05 ± 0.02 | 0.1 ± 0.04 | 0.2 ± 0.09 |
| paclitaxel (a known antineoplastic compound) | 0.2 ± 0.06 | 0.0003 ± 0.0002 | 0.047 ± 0.007 | 0.001 ± 0.001 |

The anti-tumor activity of the compounds of formula I may further be demonstrated employing the hollow fiber in vivo tumor cell cultivation model in athymic (T cell deficient) nude mice. Utilizing this model, one can measure the ability of test compounds to inhibit the growth of human tumor cells in hollow fibers growing subcutaneously (s.c.) in athymic nude mice. The histologic tumor types employed were MIP 101 colon carcinoma, HCT-116 colon carcinoma, 1A9PTX22 ovarian carcinoma, and 1A9 ovarian carcinoma.

The HCT 116 human colon tumor cell line was obtained from the American Type Culture Collection, Rockville, Md. The MIP 101 human colon tumor cell line was obtained from Dr. Robert Kramer (Bristol Meyers Squibb) and was previously described (Niles R M, Wilhelm S A, Steele G D JR, Burke B, Christensen T, Dexter D, O'Brien M J, Thomas P, Zamcheck N. Isolation and characterization of an undifferentiated human colon carcinoma cell line (MIP-101). Cancer Invest. 1987;5(6):545-52.). The 1A9 and the 1A9PTX22 ovarian tumor cell lines were obtained from Dr. Toto Fojo, Medicine Branch, Division of Clinical Sciences, National Cancer Institute, National Institutes of Health, Bethesda, Md. 20892. The 1A9 is a clone of the ovarian carcinoma cell line, A2780 (Balachandran R, ter Haar E, Welsh M J, Grant S G, Day B W. The potent microtubule-stabilizing agent (+)-discodermolide induces apoptosis in human breast carcinoma cells-preliminary comparisons to paclitaxel. Anti-Cancer Drugs 1998; 9:67–76. [Errata: Anti-Cancer Drugs 1998: 9:369–370]). The 1A9PTX22 subline was isolated as an individual clone from the 1A9 cell line in a single step selection by exposure to 5 ng/mL paclitaxel in the presence of 5 μg/mL of verapamil. The 1A9PTX22 cell line was found to be 24-fold more resistant to paclitaxel than the parental 1A9. Resistance to paclitaxel was maintained after two years of culturing in drug-free media, and was attributed to the Ala$^{364}$→Thr mutation in β-tubulin that was found in the 1A9PTX22 cell line. All cell lines were propagated and expanded in RPMI 1640 medium containing 10% heat-inactivated FBS (Life Technologies, Grand Island, N.Y.) in a tissue culture incubator (37° C., controlled, humidified atmosphere containing 5% $CO_2$). Cell expansions were performed in T75 tissue culture flasks (Costar®, Corning, N.Y.). For hollow fiber preparations, cells were harvested at 70–90% confluency using 0.25% Trypsin-EDTA (Life Technologies, Grand Island, N.Y.).

PVDF hollow fibers (Spectrum, Gardena, Calif.) were soaked in 70% EtOH for 72 hours before use. After this step, all handling of fibers was done under a biological laminar flow hood using aseptic procedures. Individual fibers were flushed with 3 mL of ice-cold tissue culture media using a syringe equipped with a 20-gauge needle. Next, each fiber was filled with an appropriate cell suspension (1×10$^6$ cells/mL for the 1A9 and 1A9PTX22 cells, and 0.3×10$^6$ cells/mL for the HCT 116 and MIP 101 cells), and both ends of the fiber were sealed with a hot flat needle holder. The entire length of the fiber was then sealed into 1.5 cm microcapsules (further called "hollow fibers"), each containing approximately 15 μL of the appropriate cell suspension. After separation, individual hollow fibers were placed in 6 well

| Compound | Cell Line | Experiment #1 % T/C ± SEM | Experiment #2 % T/C ± SEM | Average % T/C | Δ Mean % Body Weight |
| --- | --- | --- | --- | --- | --- |
| Paclitaxel | HCT 116 | 2 ± 1** | 1 ± 2** | 1 | Exp. 1: None Exp. 2: None |
| Paclitaxel | MIP 101 | 113 ± 10 | 112 ± 11 | 113 | |
| Paclitaxel | 1A9 | 1 ± 3** | 53% Reg.** | 26% Reg. | |
| Paclitaxel | PTX22 | 109 ± 16 | 84 ± 8 | 97 | |
| Ex. 1 | HCT 116 | 15 ± 4** | 10 ± 3** | 13 | Exp. 1: None Exp. 2: None |
| Ex. 1 | MIP 101 | 50 ± 9** | 90 ± 9 | 70 | |
| Ex. 1 | 1A922 | 14 ± 4** | 23 ± 8** | 19 | |
| Ex. 1 | 1A9PTX22 | 6 ± 2** | 16 ± 7** | 11 | |

**P = <0.01
Paclitaxel was dosed daily for 5 days at 15 mg/kg, i.v.
Ex. 1 was dosed once at 45 mg/kg, i.v.
Reg. = regression plates (6 fibers in 5 mL media per well), and were incubated overnight at 37° C. in the tissue culture incubator.

Outbred athymic (nu/nu) female mice ("Chrls:Athymic Nude-nu", Charles River Laboratories, Wilmington, Mass.) were anesthetized with ip injections of Ketamine/Xylazine (150 mg/kg, and 12 mg/kg body weight, respectively). For the subcutaneous implantation an 11-gauge trocar containing one or two hollow fibers was inserted through an incision made with scissors at the nape of the neck of an animal, and fibers were released by retracting the trocar while depressing the plunger. This procedure was repeated until all four hollow fibers were implanted. One wound clip was used to close the skin incision. After the surgery each animal received a single, subcutaneous injection of 0.4 mg/kg butorphenol to relieve any potential pain. Animals recovered from the anesthesia on a heating pad, before returning to their cages.

One day after the implantation (4 hollow fibers/animal, each hollow fiber containing one cell line: HCT 116, MIP 101, 1A9, and 1A9PTX22) animals were randomly sorted into five groups of six mice/group. The first group was sacrificed, hollow fibers were retrieved, and processed according to a published procedure, to determine the number of viable cells in each fiber ($T_0$.)

The remaining groups were treated as follows:
  Group 1: Example 1, 45 mg/kg, iv, once.
  Group 2: Vehicle for Example 1 (16.7% Cremophor EL, 8.3% ethanol, 75% D5W), iv, once.
  Group 3: Paclitaxel, 15 mg/kg, iv, daily for 5 days.
  Group 4: Vehicle for paclitaxel (12.5% Cremophor EL, 12.5% ethanol, 75% D5W) iv, daily for 5 days.

On day 7 all animals were sacrificed, and hollow fibers were retrieved and processed according to a published procedure, to determine the number of viable cells in each fiber (T—for fibers from animals treated with experimental compounds, C—for fibers from animals treated with corresponding vehicles). Antitumor activity was expressed as % Mean ΔT/Mean ΔC [comparing cell growth for treatment group to vehicle control group, where % Mean ΔT/Mean ΔC=(Mean T−Mean $T_0$/Mean C−Mean $T_0$)×100%]. Regressions were calculated using the formula: (1−Mean T/Mean $T_0$)×100%. Statistical significance of the results was uniformly evaluated using a two-tailed Student's t-test, as recommended by a statistician, following analysis of our representative experiments (Colin Goodal, statistical consultant to Novartis, personal communication).

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered parenterally, e.g., intraperitoneally, intravenously, intramuscularly, subcutaneously, intratumorally, or rectally, or enterally, e.g., orally, preferably intravenously or orally, more preferably intravenously at a single dosage of 1–300 mg/kg body weight per cycle (cycle=3–6 weeks) or, for most larger primates, a single dosage of 50–5000 mg per treatment cycle. A preferred intravenous single dosage per 3–6 week treatment cycle is 1–75 mg/kg body weight or, for most larger primates, a daily dosage of 50–1500 mg. A typical intravenous dosage is 45 mg/kg, once every three weeks.

Usually, a small dose is administered initially and the dosage is gradually increased until the optimal dosage for the host under treatment is determined. The upper limit of dosage is that imposed by side effects and can be determined by trial for the host being treated.

The compounds of formula I may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The compounds of formula I may be formulated into enteral and parenteral pharmaceutical compositions containing an amount of the active substance that is effective for inhibiting tumors, such compositions in unit dosage form and such compositions comprising a pharmaceutically acceptable carrier.

The following example shows a representative compound encompassed by this invention and its synthesis. However, it should be clearly understood that it is for purposes of illustration only.

EXAMPLE

Synthesis of (2R,3S,4S,5S,7S,8Z,10S,11S,12S,13Z,16S, 17S,18S,19S,20S,21Z)-19-[(aminocarbonyl)oxy]-3,5,7,11, 17-pentahydroxy-2,4,10,12,14,16,18,20-octamethyl-8,13, 21,23-tetracosatetraenoic acid, sodium salt.

A 25 mL round-bottomed flask is fitted with magnetic stirring and a septum, and maintained under a nitrogen atmosphere. The flask is charged with 95 mg (0.16 mmol) 6-[(2S,3Z,5S,6S,7S,8Z,11S,12R,13S,14S,15S,16Z)-14-[(aminocarbonyl)oxy]-2,6,12-trihydroxy-5,7,9,11,13,15-hexamethyl-3,8,16,18-nonadecatetraenyl]tetrahydro-4-hydroxy-3,5-dimethyl-(3R,4S,5R,6S)-2H-pyran-2-one [Chemical Abstracts number: 127943-53-7] and 6 mL of THF. After stirring and dissolving the solid, the flask is cooled in an ice bath. 1.6 mL of 0.10 M NaOH (0.16 mmol) is added with a syringe over about 25 minutes. After allowing the mixture to warm to room temperature, TLC showed the reaction is complete (TLC showed no starting material. TLC conditions: Eluent, 100% EtOAc; Visualization, Vanillan/$H_2SO_4$/EtOH+heat; $R_f$=0.5.). The mixture is partitioned between t-BuOMe (30 mL) and water (30 mL). The layers are separated and the product containing aqueous layer is washed with another 30 mL portion of t-BuOMe. The cloudy aqueous layer is filtered. The filtrate is rotoevaporated to obtain a white residue. The residue is reconstituted in about 30 mL water and freeze dried to afford 92 mg of the desired product as a white solid (91% yield).

$^1$H NMR (300 MHz, $D_2O$) δ6.75 (1H, dd, J=16.8, 11.0 Hz), 6.22 (1H, t, J=11.2, Hz), 5.65 (1H, t, J=9.4 Hz), 5.51 (2H, m), 5.38 (1H, d, J=16.8 Hz), 5.29 (1H, d, J=10.1 Hz), 5.02 (1H, d, J=10.1 Hz), 4.75 (1H, dd, J=10.3, 2.2 Hz), 4.53 (1H, t, J=9.0 Hz), 4.11 (1H, q, J=4.9Hz), 3.82 (1H, q, J=4.5 Hz), 3.34–3.23 (2H, m), 3.16 (1H, m), 2.71 (1H, m), 2.51 (1H, m), 2.32 (1H, m), 1.94–1.72 (4H, m), 1.71–1.55 (5H, m), 1.32 (1H, m), 1.11 (3H, d, J=6.7 Hz), 1.07 (3H, d, J=6.7 Hz), 1.02 (3H, d, J=6.7 Hz), 0.97 (3H, d, J=6.7 Hz), 0.88 (3H, d, J=6.7 Hz), 0.87 (3H, d, J=6.7 Hz), 0.80 (3H, d, J=4.5 Hz).

What is claimed is:

1. A compound of formula I

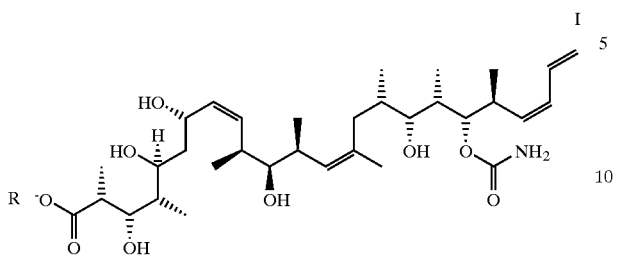

where R is Li$^+$, Na$^+$, K$^+$, ½Ca$^{++}$, ½Mg$^{++}$, ½Mn$^{++}$, R$_1$R$_2$R$_3$R$_4$N$^+$, or a nitrogen containing ring selected from

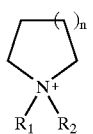 II

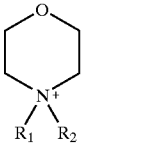 III and

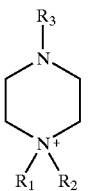 IV where each of R$_1$, R$_2$, R$_3$ and R$_4$, independently, is hydrogen, (C$_{1-12}$)alkyl, hydroxy(C$_{2-8}$)alkyl or benzyl; and n is 1–5.

2. A compound according to claim 1 of formula I where R is Li$^+$, Na$^+$, K$^+$, ½Ca$^{++}$, R$_1$R$_2$R$_3$R$_4$N$^+$, or a nitrogen containing ring selected from II, III, and IV where each of R$_1$, R$_2$, R$_3$ and R$_4$, independently, is hydrogen, (C$_{1-8}$)alkyl, hydroxy(C$_{2-6}$)alkyl or benzyl; and n is 1–3.

3. A compound according to claim 2 of formula I where R is Na$^+$, K$^+$, ½Ca$^{++}$, R$_1$R$_2$R$_3$R$_4$N$^+$, or a nitrogen containing ring selected from II and III where each of R$_1$, R$_2$, R$_3$ and R$_4$, independently, is hydrogen, (C$_{1-6}$)alkyl, hydroxy(C$_{2-4}$)alkyl or benzyl; and n is 1 or 2.

4. A compound according to claim 3 of formula I where R is Na$^+$, ½Ca$^{++}$, R$_1$R$_2$R$_3$HN$^+$, or a nitrogen containing ring selected from

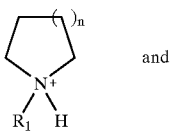 IIa and

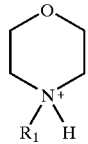 IIIa where each of R$_1$, R$_2$ and R$_3$, independently, is hydrogen, (C$_{1-6}$)alkyl, hydroxyethyl or benzyl; and n is 1 or 2.

5. A compound according to claim 1 which is (2R,3S,4S,5S,7S,8Z,10S,11S,12S,13Z,16S,17S,18S,19S,20S,21Z)-19-[(aminocarbonyl)oxy]-3,5,7,11,17-pentahydroxy-2,4,10,12,14,16,18,20-octamethyl-8,13,21,23-tetracosatetraenoic acid, sodium salt.

6. A pharmaceutical composition comprising a pharmaceutical acceptable carrier or diluent and a therapeutically effective amount of a compound according to claim 1.

7. A pharmaceutical composition comprising a pharmaceutical acceptable carrier or diluent and a therapeutically effective amount of a compound according to claim 2.

8. A pharmaceutical composition comprising a pharmaceutical acceptable carrier or diluent and a therapeutically effective amount of a compound according to claim 3.

9. A pharmaceutical composition comprising a pharmaceutical acceptable carrier or diluent and a therapeutically effective amount of a compound according to claim 4.

10. A pharmaceutical composition according to claim 6 comprising a pharmaceutical carrier or diluent and a therapeutcially effective amount of (2R,3S,4S,5S,7S,8Z,10S,11S,12S,13Z,16S,17S,18S,19S,20S,21Z)-19-[(aminocarbonyl)oxy]-3,5,7,11,17-pentahydroxy-2,4,10,12,14,16,18,20-octamethyl-8,13,21,23-tetracosatetraenoic acid, sodium salt.

11. A method of treating tumors selected from the group consisting of lymphoma, sarcoma, carcinoma, myeloma and leukemia cell lines comprising administering to a mammal in need of such treatment a therapeutically effective amount of a compound according to claim 1.

12. A method of treating tumors selected from the group consisting of lymphoma, sarcoma, carcinoma, myeloma and leukemia cell lines comprising administering to a mammal in need of such treatment a therapeutically effective amount of a compound according to claim 2.

13. A method of treating tumors selected from the group consisting of lymphoma, sarcoma, carcinoma, myeloma and leukemia cell lines comprising administering to a mammal in need of such treatment a therapeutically effective amount of a compound according to claim 3.

14. A method of treating tumors selected from the group consisting of lymphoma, sarcoma, carcinoma, myeloma and leukemia cell lines comprising administering to a mammal in need of such treatment a therapeutically effective amount of a compound according to claim 4.

15. A method according to claim 11 comprising administering to a mammal in need of such treatment a therapeutically effective amount of (2R,3S,4S,5S,7S,8Z,10S,11S,12S,13Z,16S,17S,18S,19S,20S,21Z)-19-[(aminocarbonyl)oxy]-3,5,7,11,17-pentahydroxy-2,4,10,12,14,16,18,20-octamethyl -8,13,21,23-tetracosatetraenoic acid, sodium salt.

16. A process for preparing a compound according to claim 1 which comprises hydrolyzing a compound having the formula

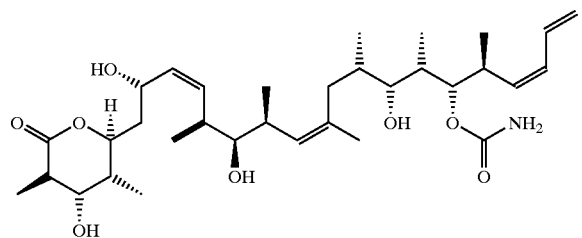
with ROH, where R is as defined in claim 1, in the presence of a polar organic solvent.
17. A process according to claim 16 wherein the solvent is an ether and the hydrolysis is carried out at a temperature of between 0° C. and 20° C.
18. A process according to claim 17 wherein the solvent is tetrahydrofuran and the hydrolysis is carried out at a temperature of between 0° C. and 10° C.
* * * * *